(12) United States Patent
Montgomery

(10) Patent No.: US 9,987,173 B1
(45) Date of Patent: Jun. 5, 2018

(54) MALE DIAPER WITH SEALABLE FRONT OPENING

(71) Applicant: Annette Montgomery, Davis, CA (US)

(72) Inventor: Annette Montgomery, Davis, CA (US)

(*) Notice: Subject to any disclaimer, the term of this patent is extended or adjusted under 35 U.S.C. 154(b) by 268 days.

(21) Appl. No.: 14/978,949

(22) Filed: Dec. 22, 2015

Related U.S. Application Data

(60) Provisional application No. 62/187,702, filed on Jul. 1, 2015.

(51) Int. Cl.
| | | |
|---|---|---|
| A61F 13/15 | (2006.01) | |
| A61F 13/491 | (2006.01) | |
| A61F 13/49 | (2006.01) | |
| A61F 13/56 | (2006.01) | |
| A61F 13/62 | (2006.01) | |

(52) U.S. Cl.
CPC .... *A61F 13/4915* (2013.01); *A61F 13/49011* (2013.01); *A61F 13/565* (2013.01); *A61F 13/622* (2013.01)

(58) Field of Classification Search
CPC ............ A61F 13/4915; A61F 13/49011; A61F 13/565; A61F 13/622
USPC ........................................................ 604/349
See application file for complete search history.

(56) References Cited

U.S. PATENT DOCUMENTS

| | | | |
|---|---|---|---|
| 4,944,733 A | 7/1990 | Casale | |
| 6,409,712 B1* | 6/2002 | Dutari | A61F 13/471 604/349 |
| 7,434,273 B2* | 10/2008 | Chung | A41B 9/023 2/403 |
| 8,118,798 B1* | 2/2012 | Campbell | A61F 13/471 604/349 |
| 8,702,667 B1* | 4/2014 | Johnson | A61F 13/471 604/349 |
| 2007/0043329 A1* | 2/2007 | Evans | A61F 5/449 604/349 |
| 2013/0274699 A1 | 10/2013 | Kelley et al. | |
| 2017/0135875 A1* | 5/2017 | Johnson | A41B 9/02 |

* cited by examiner

*Primary Examiner* — Jacqueline Stephens
(74) *Attorney, Agent, or Firm* — Plager Schack LLP

(57) ABSTRACT

A male diaper permits a user to urinate without removing the diaper from a lower body region of the user and includes a main body member disposed around the lower body region of the user and having a front portion with a crotch region having a front flap and a rear flap separated to create an opening to permit the user's reproductive organ to pass therethrough, and an exterior flap detachably coupled to the front portion of the main body member by a fastener. The exterior flap is designed to attach to the main body member to a closed position to seal the opening. The exterior flap is designed to detach from the main body member to an open position to permit the reproductive organ of the user to extend through the opening and into a surrounding environment, thereby enabling the user to urinate.

4 Claims, 4 Drawing Sheets

MALE DIAPER WITH SEALABLE FRONT OPENING

RELATED APPLICATION

The application claims priority to provisional patent application U.S. Ser. No. 62/187,702 filed on Jul. 1, 2015, the entire contents of which is herein incorporated by reference.

BACKGROUND

The embodiments herein relate generally to diapers.

Many male diapers are disadvantageous because a user has to unbutton or unzip his pants, and pull down the pants and diaper prior to urinating. These required steps and a delay in timing may cause individuals to soil their clothes, pants and/or diaper. This can be especially problematic for those individuals suffering from incontinence.

Several diapers exist with a closeable opening as disclosed in U.S. Pat. No. 4,944,733 and U.S. Patent Application Publication 2013/0274699. Although these diapers permit the user to use the toilet without pulling down the diaper, they have several disadvantages. First, these diapers comprise sealable flaps positioned directly above the user's male reproductive organ when worn. These flaps are secured by fasteners such as hook and loop fasteners or tape fasteners. This assembly is undesirable because the user's reproductive organ and/or pubic hair can get caught in the fasteners of the sealable flaps, which can cause pain to the user. Second, the openings in several of the diapers are sufficiently large to expose the genitals and anus of the user. This may cause the user to suffer discomfort, embarrassment and/or a loss of dignity when the diaper flap is opened in the presence of others.

As such, there is a need in the industry for a male diaper with a sealable opening, which permits a user to urinate without removing the diaper from its original position on the body while enhancing user comfort and dignity. This allows the user to pull up or pull down the diaper with ease. In addition, there is a need for a male diaper that prevents the user's reproductive organ and/or public hair from becoming caught in any fasteners used to seal the diaper opening.

SUMMARY

A male diaper for use in permitting a user to urinate without removing the diaper from a lower body region of the user is provided. The male diaper comprises a sealable opening configured to minimize a likelihood that a male reproductive organ or pubic hair becomes caught within a fastener coupled to the sealable opening. The male diaper comprises a main body member disposed around the lower body region of the user and comprising a front portion, side portions and a rear portion opposite the front portion, the front portion comprising a crotch region comprising a front flap and a rear flap positioned proximate the reproductive organ of the user, the front flap and rear flap separated to create an opening configured to permit the reproductive organ of the user to pass therethrough, and an exterior flap detachably coupled to the front portion of the main body member by the fastener, wherein the exterior flap is configured to attach to the main body member to a closed position to seal the opening, wherein the exterior flap is configured to detach from the main body member to an open position to permit the reproductive organ of the user to extend through the opening and into a surrounding environment, thereby enabling the user to urinate.

BRIEF DESCRIPTION OF THE FIGURES

The detailed description of some embodiments of the invention will be made below with reference to the accompanying figures, wherein the figures disclose one or more embodiments of the present invention.

DETAILED DESCRIPTION OF CERTAIN EMBODIMENTS

Figure 1:
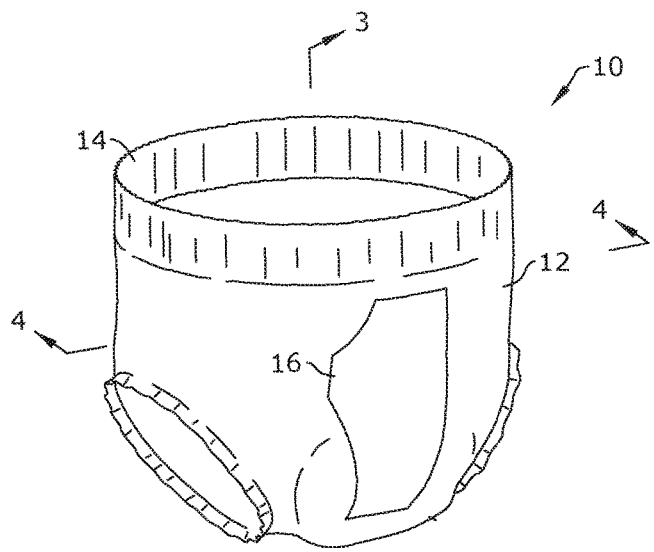
FIG. 1 depicts a perspective view of certain embodiments of the male diaper with exterior flap 16 in a closed position.
Figure 2:
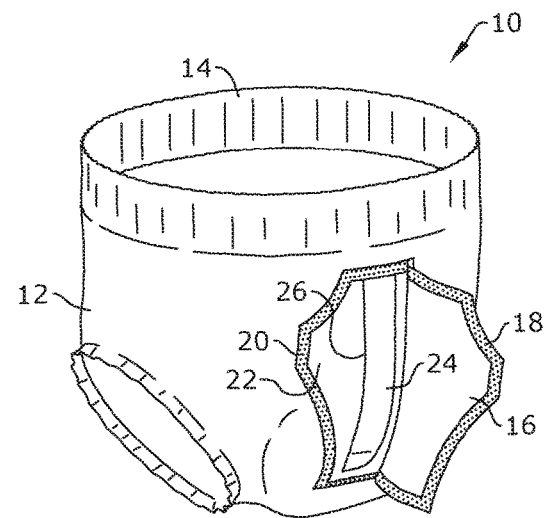
FIG. 2 depicts a perspective view of certain embodiments of the male diaper with exterior flap 16 in an open position.
Figure 3:
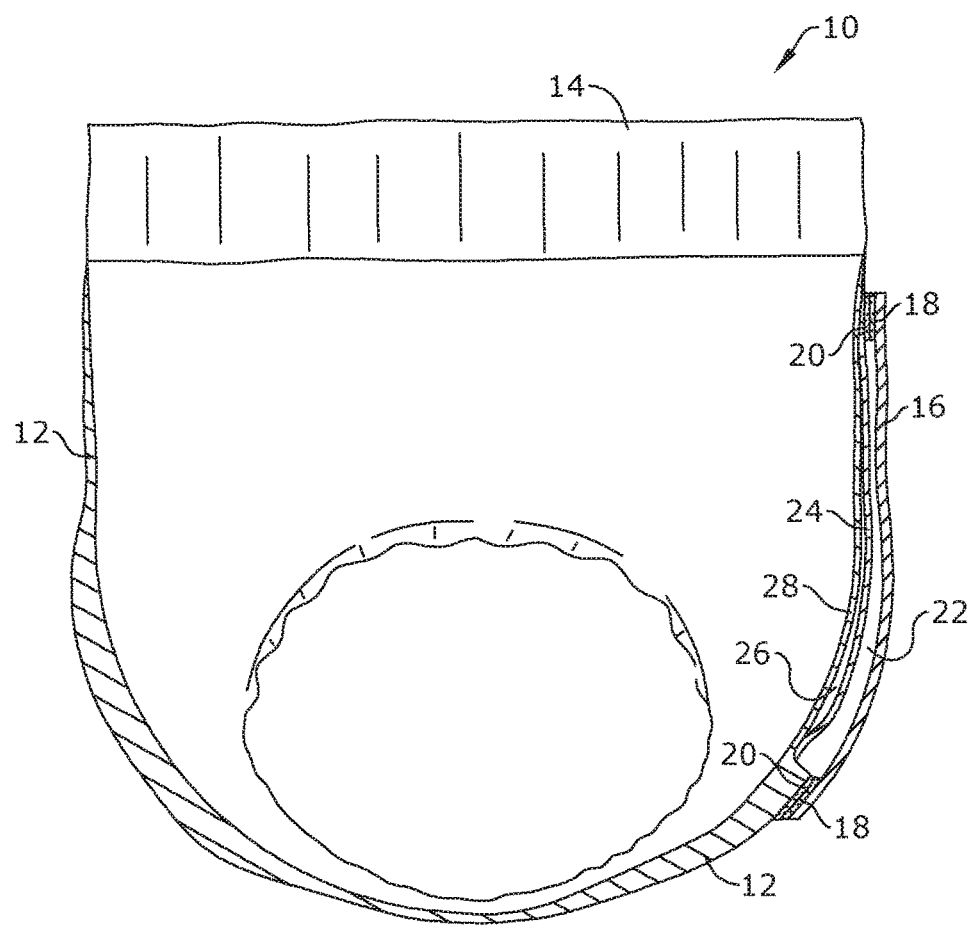
FIG. 3 depicts a section view of certain embodiments of the male diaper taken along line 3-3 in FIG. 1.
Figure 4:
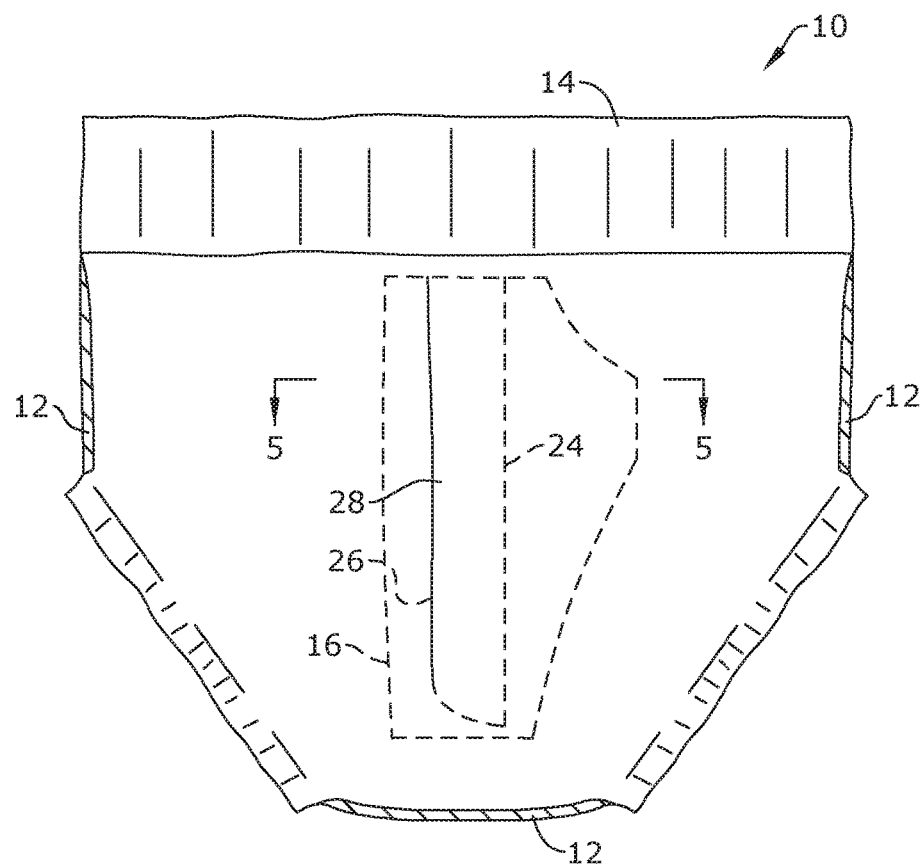
FIG. 4 depicts a section view of certain embodiments of the male diaper taken along line 4-4 in FIG. 1.

As depicted in FIGS. 1-4, diaper 10 is configured for use by a male user (not shown) to permit the user to urinate without requiring the diaper to be pulled down or repositioned. In addition, diaper 10 is designed to prevent the user's reproductive organ and/or pubic hair from getting caught in any fasteners present thereon. Diaper 10 generally comprises main body member 12, waistband 14, exterior flap 16, front fly flap 24 and rear fly flap 28.

Main body member 12 comprises an upper opening disposed around the user's waist and a pair of lower openings to permit the user's legs to pass through. In one embodiment, waistband 14 is enclosed within the top portion of main body member 12. This enables waistband 14 to tightly conform around the user's waist to prevent diaper 10 from sliding out of position once properly secured in place. Waistband 14 may comprise any elastic, stretchable and/or resilient material known in the field such as rubber.

The front portion of main body member 12 comprises a crotch region having front fly flap 24 and rear fly flap 28. These fly flaps 24, 28 may have reinforced edges and be attached together by stitching. Space between front fly flap 24 and rear fly flap 28 creates fly opening 26, which is configured to permit the user's reproductive organ to pass through.

Exterior flap 16 comprises an edge coupled to the front portion of main body member 12 by a fastening component such as stitching. Exterior flap 16 may be opened to create exterior flap opening 22 or closed to seal exterior flap opening 22 and fly opening 26. In a preferred embodiment, exterior flap 16 comprises hook fastener 18 disposed along an interior edge of the flap. A corresponding loop fastener 20 is coupled to the front portion of main body member 12. This permits hook fastener 18 to engage with loop fastener 20 when exterior flap 16 is in the closed position. In an alternative embodiment, loop fastener 20 and hook fastener 18 may be interchanged. It shall be appreciated that any alternative fastening components known in the field can be used instead such as snap components, zippers, buttons, or the like.

In a preferred embodiment, main body member 12, front fly flap 24, rear fly flap 28 and exterior flap 16 are made from a non-woven fabric material that is capable of absorbing fluid and preventing leaks. However, any alternative material or combination of materials known in the field may be used instead.

Figure 5:
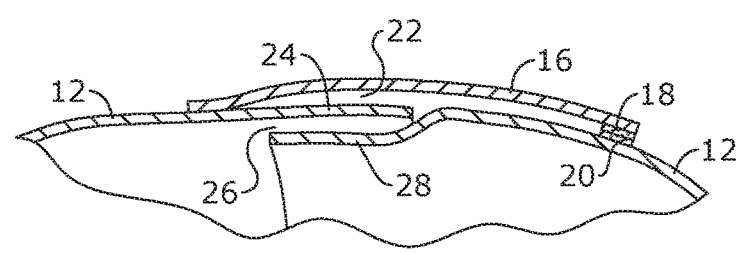
FIG. 5 depicts a section view of certain embodiments of the male diaper.
Figure 6:
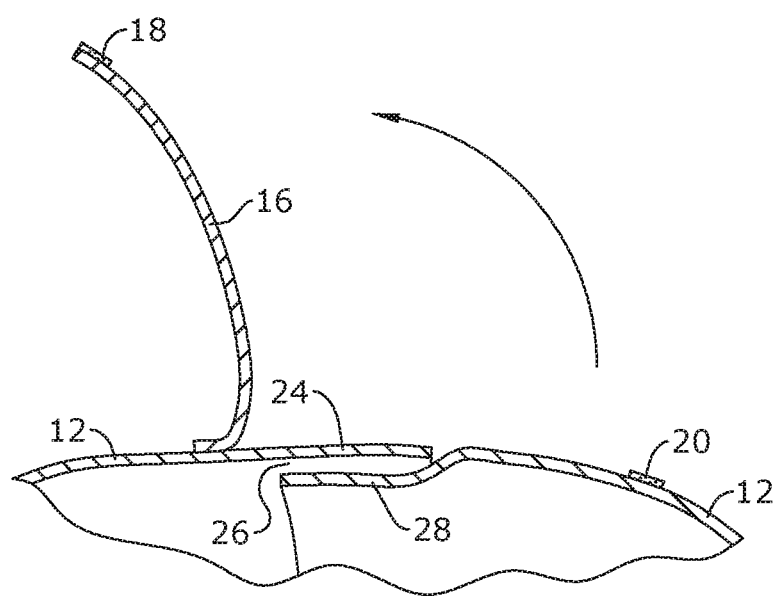
FIG. 6 depicts a section view of certain embodiments of the male diaper illustrating the opening of exterior flap 16 to expose fly opening 26.

In operation, diaper 10 is worn by the user (not shown). Rear fly flap 28, front fly flap 24 and exterior flap 16 are positioned generally above the user's reproductive organ. As depicted in FIG. 5, exterior flap 16 is in the closed position with hook fastener 18 engaged with loop fastener 20 on main body member 12. In this closed position, front fly flap 24 and rear fly flap 28 serve as a barrier that shields the user's reproductive organ and pubic hair from hook fastener 18 and/or loop fastener 20. This minimizes the chance the user's reproductive organ or pubic hair gets caught in these fasteners and causes pain or discomfort. If the user needs to urinate, exterior flap 16 is detached from main body member 12 and adjusted to the open position as shown in FIG. 6. This permits the user's reproductive organ to extend through fly opening 26 and exterior flap opening 22 to the outside environment to permit the user to urinate. Once urination is completed, the user can retract his reproductive organ within diaper 10 and reseal exterior flap 16 to the closed position as shown in FIGS. 1 and 5.

It shall be appreciated that diaper 10 is advantageous because the user does not have to pull down or remove the diaper when he has to urinate. In addition, the user's reproductive organ is shielded from fasteners 18, 20 by fly flaps 24, 28. This enhances user comfort, safety and dignity when diaper 10 is worn. It shall be appreciated that the components of diaper 10 described in several embodiments herein may comprise any alternative known materials in the field and be of any color, size and/or dimensions. It shall be appreciated that the components of diaper 10 described herein may be manufactured and assembled using any known techniques in the field.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A male diaper for use in permitting a user to urinate without removing the diaper from a lower body region of the user, the male diaper comprising a sealable opening configured to minimize a likelihood that a male reproductive organ or pubic hair becomes caught within a fastener coupled to the sealable opening, the male diaper comprising:
    a main body member configured to be disposed around the lower body region of the user and comprising a front portion, side portions and a rear portion opposite the front portion, the front portion comprising a crotch region comprising a front flap and a rear flap configured to be positioned adjacent to the reproductive organ of the user, the front flap and rear flap extending in opposite directions and separated to create an opening configured to permit the reproductive organ of the user to pass therethrough; and
    an exterior flap coupled to the front portion of the main body member by the fastener and comprising a top edge, a bottom edge opposite the top edge, and a pair of side edges connecting the top and bottom edges together, one of the side edges in the pair of side edges in the exterior flap coupled to the front portion of the main body member to permit the exterior flap to pivot laterally around the side edge coupled to the main body member, wherein the exterior flap is maneuverable to attach to the main body member to a closed position to seal the opening, wherein the exterior flap is maneuverable to detach from the main body member to an open position that is configured to permit a reproductive organ of the user to extend through the opening and into a surrounding environment, thereby enabling the user to urinate.

2. The male diaper of claim 1, further comprising an elastic band enclosed within upper portions of the front portion, side portion and rear portion of the main body member, wherein the elastic band is configured to conform to a waist region of the user.

3. The male diaper of claim 2, wherein the fastener comprises a hook fastener disposed along edges of the exterior flap and a corresponding loop fastener disposed on the front portion of the main body member, wherein the hook fastener is configured to engage with the loop fastener.

4. A male diaper for use in permitting a user to urinate without removing the diaper from a lower body region of the user, the male diaper comprising a sealable opening configured to minimize a likelihood that a male reproductive organ or pubic hair becomes caught within a fastener coupled to the sealable opening, the male diaper comprising:
    a main body member configured to be disposed around the lower body region of the user and comprising a front portion, side portions and a rear portion opposite the front portion, the front portion comprising a crotch region comprising a front flap and a rear flap configured to be positioned adjacent to the reproductive organ of the user, the front flap and rear flap extending in opposite directions and separated to create an opening configured to permit the reproductive organ of the user to pass therethrough; and
    an exterior flap coupled to the front portion of the main body member by the fastener and comprising a top edge, a bottom edge opposite the top edge, and a pair of side edges connecting the top and bottom edges together, one of the side edges in the pair of side edges in the exterior flap coupled to the front portion of the main body member to permit the exterior flap to pivot laterally around the side edge coupled to the main body member, wherein the exterior flap is maneuverable to attach to the main body member to a closed position to seal the opening and enclose the front and rear flaps of the main body member, wherein the exterior flap is maneuverable to detach from the main body member to an open position that is configured to permit a reproductive organ of the user to extend through the opening and into a surrounding environment, thereby enabling the user to urinate.

\* \* \* \* \*